(12) United States Patent
Schadt et al.

(10) Patent No.: US 6,546,819 B1
(45) Date of Patent: Apr. 15, 2003

(54) APPARATUS FOR SAMPLING FLUID FROM REACTOR VESSEL

(75) Inventors: John C. Schadt, Watertown, WI (US); Michael D. Farrell, Brookfield, WI (US)

(73) Assignee: Sentry Equipment Corporation, Oconomowoc, WI (US)

( * ) Notice: Subject to any disclaimer, the term of this patent is extended or adjusted under 35 U.S.C. 154(b) by 283 days.

(21) Appl. No.: 09/634,360

(22) Filed: Aug. 9, 2000

Related U.S. Application Data

(63) Continuation-in-part of application No. 09/373,450, filed on Aug. 12, 1999, now Pat. No. 6,205,869.

(51) Int. Cl.$^7$ .................................................. G01N 1/00
(52) U.S. Cl. ..................................... 73/863.71; 137/423
(58) Field of Search .......................... 73/863.71, 863.72, 73/863.81, 863.83, 863.85, 863.86, 864.34, 864.73, 864.74, 864.63; 137/409, 423, 428–430, 433, 434, 439

(56) References Cited

U.S. PATENT DOCUMENTS

| | | | |
|---|---|---|---|
| 2,767,552 A | * 10/1956 | Clute | 137/428 |
| 3,798,972 A | 3/1974 | Collins, Jr. | 73/422 |
| 4,628,749 A | 12/1986 | Rafter, Jr. | 73/863.71 |
| 5,029,485 A | 7/1991 | Marr | 73/864.34 |
| 5,296,197 A | 3/1994 | Newberg et al. | 422/103 |
| 5,408,889 A | 4/1995 | Parault | 73/863.71 |

FOREIGN PATENT DOCUMENTS

| | | | |
|---|---|---|---|
| GB | 1360346 | 7/1974 | 73/863.83 |

OTHER PUBLICATIONS

Marketing Product Update, Grinnell Corporation, PV Reactor Sampling Systems for Continuous Media Circulation and PH Monitoring.
Technova, Safesamp, Reactor Sampling Systems RSS Series—No Date.

* cited by examiner

*Primary Examiner*—Robert Raevis
(74) *Attorney, Agent, or Firm*—Jansson, Shupe & Munger, Ltd.

(57) ABSTRACT

A fluid-sampling apparatus is disclosed. The apparatus includes a valve assembly, an overflow chamber assembly, a vacuum assembly and a sample bottle mounting assembly in particular arrangements. In certain preferred embodiments the overflow chamber assembly has an inner vessel, preferably a standpipe, within an outer vessel which forms an overflow chamber in which fluid from the standpipe can be viewed. The valve assembly preferably includes a sampling valve with an outer shell, an insert member and a pivotable valve member therein. The pivotable valve member preferably has a main body portion with first and second circumferential grooves therein and a diagonal bore therethrough for properly directing fluid from and through particular ports in the insert member based on the position of the valve member. The method includes drawing the fluid from the reactor vessel through a valve assembly into an inner vessel of an overflow chamber assembly, overflowing the fluid from the inner vessel into an outer vessel of the overflow chamber assembly, and thereafter retrieving a sample from the inner vessel.

19 Claims, 12 Drawing Sheets

APPARATUS FOR SAMPLING FLUID FROM REACTOR VESSEL

RELATED APPLICATION

This application is a continuation-in-part of U.S. patent application Ser. No. 09/373,450, filed Aug. 12, 1999, entitled "Apparatus and Method for Sampling Fluid from Reactor Vessel, now U.S. Pat. No. 6,205,869.

FIELD OF THE INVENTION

The present invention generally relates to the sampling of fluid for testing and, more particularly, to an apparatus and methods for periodically sampling fluids from reactor vessels while reactions are in progress.

BACKGROUND OF THE INVENTION

A variety of systems for sampling fluids from reactors and tanks are known. However, numerous disadvantages and shortcomings exist with prior systems, and there is a need for improvement to overcome such disadvantages and shortcomings.

Some examples of commercially-available prior fluid-sampling devices are the "Safesamp Reactor Sampling Systems" sold by Technova AG, of Sweden, and the "Neotecha Sampling Systems" sold by Grinnell Corporation, of Exeter, N.H.

The Safesamp system's basic arrangement includes a flanged dip pipe for connection to the tank with the dip pipe extending downwardly into the fluid in the tank, a bottom flange with a suction hose mounted at the top and extending downward through the dip pipe and into the tank fluid and a perpendicular connection port in communication with the dip pipe to pressurize the tank. The bottom flange is connected to a flanged "charging" ball valve. A middle flange is connected to the charging valve and has a sightglass with a ball float mounted on top and a perpendicular port located below the sightglass to direct flow for sampling. An upper flange is mounted on top of the sightglass and includes the sightglass ball seat, perpendicular connections for auxiliaries and a perpendicular port for a vent return. The perpendicular sampling port located in the middle flange is connected to a flanged isolation ball valve which is connected to the sampling assembly. The sampling assembly includes a sample bottle which is vented through another isolation ball valve which is connected to the vent return port in the upper flange.

To obtain a sample, the "charging" ball valve is opened (the sampling isolation valve is closed) and the fluid is drawn up through the suction tube (by supplying, if needed, a vacuum via the upper flange connection or pressurizing the tank via the lower flange connection). The fluid flows upwardly, fills the perpendicular sampling port in the middle flange (to the isolation ball valve) and continues filling the sightglass. As fluid fills the sightglass, the ball float rises with the level until it reaches the top of the sightglass where the ball then seats against the ball seat located in the upper flange and flow stops. The operator closes the "charging" ball valve and opens the sampling isolation valve and the vent valve. The fluid flows by gravity from the sightglass through the perpendicular sampling port in the middle flange, through the sampling isolation valve and into the sample bottle. Any entrapped gases are vented through the vent connection located between the sampling bottle and the vent return line.

The above-described sampling system has drawbacks in that the sample fluid volume would consist of partial previous sampling fluid if the system is not purged after each sampling, or would nonetheless consist of the first volume of fluid that is drawn from the top of the tank without any system fluid flushing first. It would be preferable to drain off the first and perhaps subsequent volumes of fluid so that the fluid sent to the sampling bottle is a sample that has not been mixed with previous samples or other contaminants. Such sampling system can only get an unmixed sample within the sampling bottle by drawing numerous cycles of fluid through the system. This is a time-consuming and inconvenient process, and is wasteful of the often expensive chemicals being mixed in the reactor vessel.

The aforementioned Neotecha systems, sold by Grinnell Corporation, are generally similar to the above-described Safesamp Samplers. The Neotecha system samples fluid from reactors for continuous media circulation and pH monitoring. The Neotecha samplers utilize double-diaphragm pumps and are relatively compact in design. The Neotecha samplers also use lined stainless steel braided hoses and connections to facilitate quick start-ups and convenient changes. They have a pH probe connection device which allows adaptation to most commercially-available pH probes, and various auxiliary ports to facilitate cleaning of wetted surfaces and additional vessel access.

However, the Neotecha systems have the problem that, when chemical compositions in the reactor vessel have particulates or become viscous to some extent, the compositions can tend to clog or damage the pump. This leads to costly down time for cleaning and repair.

These and other existing devices for sampling fluids from reactor vessels have significant problems. This invention addresses and overcomes such problems.

OBJECTS OF THE INVENTION

An object of the present invention is to provide an improved fluid-sampling apparatus which easily and reliably gives properly-representative samples from a reactor vessel.

Another object of this invention is to provide an improved in-process fluid-sampling apparatus which is reliably useful for a wide variety of reaction fluids, including mixtures with significant particulates and/or raised viscosities.

Yet another object of this invention is to provide an improved fluid-sampling apparatus which gives reliably-representative samples quickly, without any need for repeated withdrawal of fluids from the reactor vessel.

Another object of the invention is to provide an improved fluid-sampling apparatus which avoids waste of valuable reaction fluids.

Another object of the invention is to provide an improved fluid-sampling apparatus which avoids or minimizes significant downtime for cleaning and repair and which is easy to flush for cleaning and easy to disassemble for repair.

Still another object of the invention is to provide an apparatus for sampling fluid from a reactor vessel without contaminating the vacuum source used to draw the sample, while at the same time not requiring flushing of the sample or multiple cycling of the sample through a sight glass.

Another object of the invention is to provide improved fluid-sampling methods which overcome certain problems of existing methods and apparatus.

SUMMARY OF THE INVENTION

In accordance with the present invention, a vacuum assembly is provided for drawing fluid into an interior of an overflow tank from a fluid source. The vacuum assembly includes a vacuum source and a tubular conduit having a first end operatively connected to the vacuum source and a second end disposed within the overflow tank. An overflow element is provided for preventing the flow of fluid into the conduit in response to the fluid in the overflow tank reaching a predetermined level.

The conduit may include a vacuum port spaced from the second end of the conduit and a fill port disposed at the second end of the conduit. The overflow element is positioned within the conduit and is movable between a fill position wherein the vacuum source communicates with the interior of the overflow tank and a shut-off position wherein the interior of the overflow tank is isolated from the vacuum source. The overflow element is urged from the fill position and the shut-off position by fluid in the interior of the overflow tank. It is contemplated that the overflow element include a float ball.

In accordance with a still further aspect of the present invention, a fluid-sampling apparatus is provided for sampling fluid from a fluid source. The fluid-sampling apparatus includes an overflow chamber assembly defining an overflow chamber therein. A valve assembly interconnects the overflow chamber assembly and the fluid source. The valve assembly includes a valve movable between a first position and wherein overflow chamber communicates with the fluid source and a second position. A vacuum assembly is interconnected to the overflow chamber assembly for drawing fluid from the fluid source into the overflow chamber of the valve. The vacuum assembly includes a float valve cage disposed within the overflow chamber for limiting the fluid drawn into the overflow chamber to a predetermined level.

The vacuum assembly may include a tubular conduit having a first end operatively connected to a vacuum source and a second end operatively connected to the float valve cage. A seal having a central aperture is also provided. The central aperture of the seal allows the tubular conduit to pass therethrough. The seal has a sealing flange projecting radially from the central aperture which is captured between the vacuum assembly and the overflow chamber assembly. The sealing flange includes a recess therein which extends about the central aperture in the seal.

It is contemplated that the float valve cage include a vacuum port. An overflow element is disposed within the float valve cage. The overflow element is movable between a fill position wherein a vacuum source communicates with the interior of the overflow chamber through the vacuum port and a shut-off position wherein the interior of the overflow chamber is isolated from the vacuum source. The overflow element is urged from the fill position to the shut-off position by fluid in the overflow chamber. The overflow element includes a float ball.

In accordance with a still further aspect of the present invention, a fluid-sampling apparatus is provided for sampling fluid from a fluid source. The fluid-sampling apparatus includes an overflow chamber assembly defining an overflow chamber therein. A valve assembly interconnects the overflow chamber and the fluid source. The valve assembly includes a valve movable between a first position wherein the overflow chamber communicates with the fluid source and a second position. A vacuum assembly is interconnected to the overflow chamber assembly for drawing fluid from a fluid source into the overflow chamber through the valve. The vacuum assembly includes a float valve caged disposed within the overflow chamber for limiting the fluid drawn into the overflow chamber to a predetermined level. A sample bottle having an interior is operatively connected to the valve assembly. The interior of the sample bottle communicates with the overflow chamber with the valve in the second position.

An overflow element is disposed in the float valve cage. The overflow element is movable between a fill position wherein a vacuum source communicates within the interior of the overflow chamber through the vacuum port and a shut-off position wherein the interior of the overflow chamber is isolated from the vacuum source. The overflow element is urged from the float position to the shut-off position by fluid in the overflow chamber. The overflow element includes first and second float balls.

BRIEF DESCRIPTION OF THE DRAWING FIGURES

The drawings furnished herewith illustrate a preferred construction of the present invention in which the above advantages and features are clearly disclosed as well as others which will be readily understood from the following description of the illustrated embodiment.

DETAILED DESCRIPTIONS OF PREFERRED EMBODIMENTS

Figure 1:
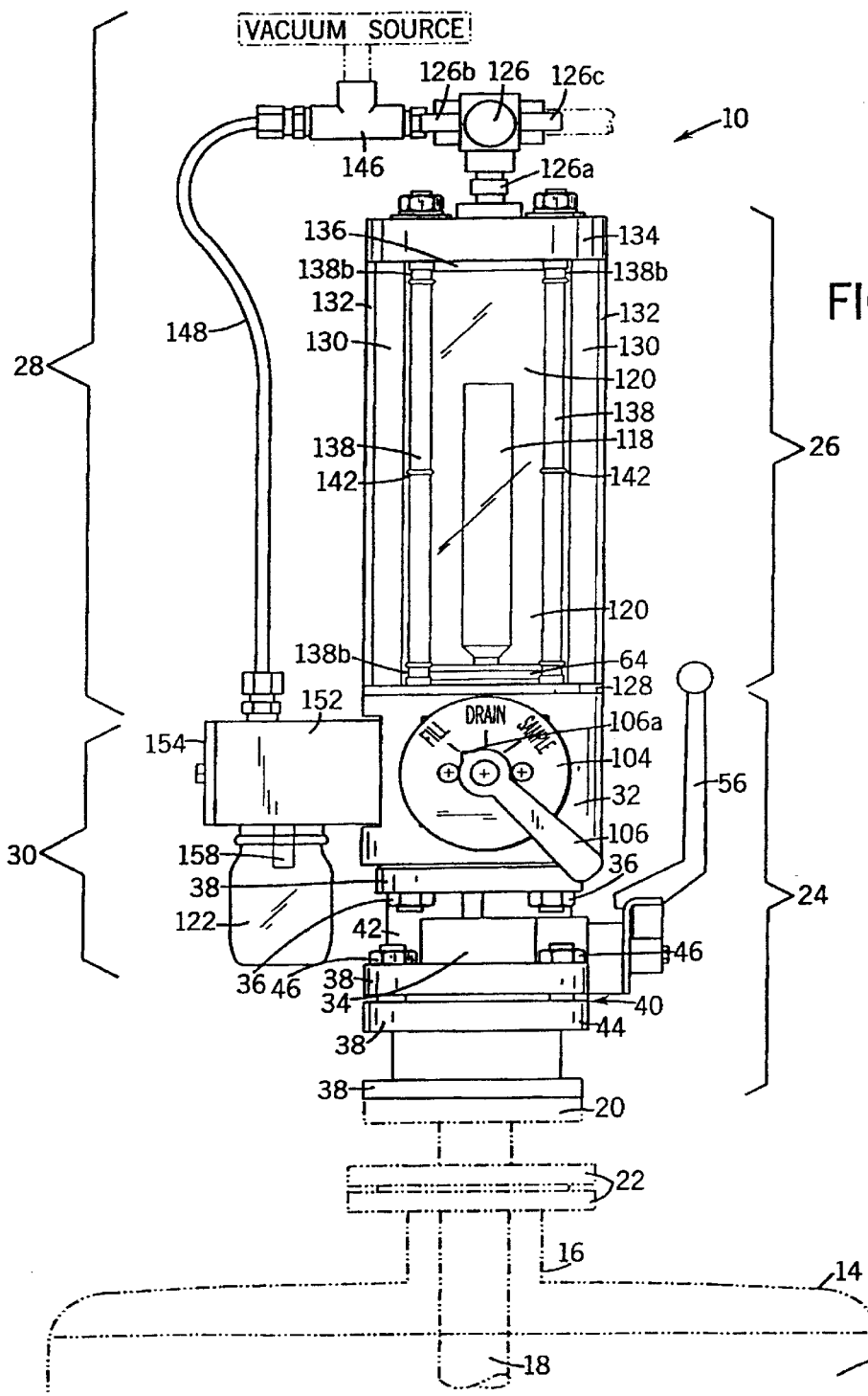
FIG. 1 is a front elevational view of a fluid-sampling apparatus in accordance with the present invention.
Figure 2:
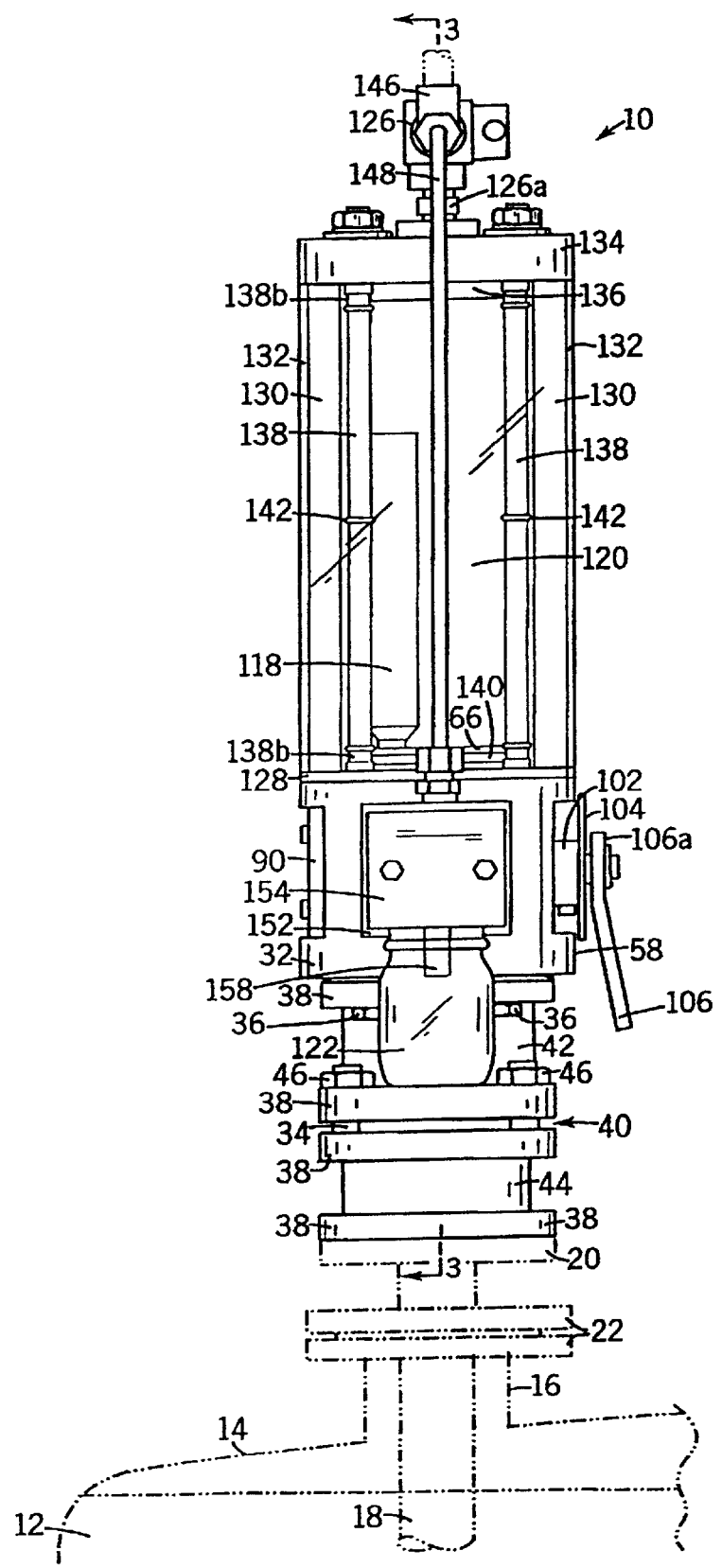
FIG. 2 is a left side elevation of the fluid-sampling apparatus of FIG. 1.

FIGS. 1 and 2 illustrate a fluid-sampling apparatus 10 for sampling fluid 12 from a reactor vessel 14. Fluid-sampling apparatus 10 is mounted on top of a sampling port 16 of reactor vessel 14. A dip tube 18, having either a single flange 20 or a double flange 22 (as denoted in dashed outline) at the top thereof, is connected to the bottom of fluid-sampling apparatus 10. Dip tube 18 extends through sampling port 16 of reactor vessel 14 into fluid 12 at the top of reactor vessel 14.

Fluid-sampling apparatus 10 includes: a valve assembly 24; a overflow chamber assembly 26; a vacuum assembly 28; and a sample bottle mounting assembly 30. Each of valve assembly 24, overflow chamber assembly 26, vacuum assembly 28, and sample bottle mounting assembly 30 is comprised of various component parts which will be explained below.

Valve assembly 24 includes a sampling valve 32 mounted on top of a ball valve 34. The bottom of sampling valve 32 is connected to the top of ball valve 34 via mating fasteners or the like in known fashion, as illustrated in several of the drawing figures.

Details of ball valve 34 will not be described, since they are well known in the art. An acceptable ball valve 34 is a Richter™ Fluoroplastic Lined Valve for Corrosive Applications (KNA Full Port Series), manufactured by ITT Engineered Valves. It is noted, however, than handle 56 of ball valve 34 controls the operation thereof, and that ball valve 34 serves typical shut-off and flow functions.

Referring now to the cross-sectional views of FIGS. 3 and 9–13, sampling valve 32, which is connected to the top of ball valve 34, will now be explained in more detail. It should be noted that the combination of sampling valve 32 and ball valve 34 provides for double block isolation from reactor vessel 14. Sampling valve 32 includes an outer shell 58 for housing an insert member 60 therewithin. Outer shell 58 has an open top for sliding insertion of insert member 60 thereinto. Outer shell 58 has front, back, left-hand side, right-hand side, and bottom surfaces. Each of the front, back, left-hand side, and bottom surfaces of shell 58 has apertures therethrough. Each of the front, back, and left-hand side surfaces of outer shell 58 of sampling valve 32 are somewhat "indented" or "two-tiered" as shown in FIGS. 1 and 2 so that flanges formed at the top and bottom of the front, back, and left-hand sides of sampling valve 32 protrude more horizontally outwardly than do the actual surface of the front, back, and left hand sides of sampling valve 32. This indented wall surface arrangement is for positioning of a member between the flanges as will be explained in more detail below.

Insert member 60 is a somewhat squarish block of material, preferably made of a virgin Teflon material, with various extensions therefrom and spaces, ports, etc. therein. More particularly, insert member 60 has an upwardly-extending top portion 64 which extends through the open top of outer shell 58 and a tubular lower portion 66. Insert member 60 has a space therein for receiving a pivotable valve member (hereafter described). Such space within insert member 60 leads from a smaller diameter opening in the front surface of insert member 60 to a larger diameter opening in the back surface of insert member 60. There are also first, second, third and fourth ports 74, 76, 78 and 80 leading from the space within insert member 60 to various positions on the outer periphery of insert member 60. Second and fourth ports 76 and 80 have widened-diameter opening portions located immediately adjacent the outer periphery of insert member 60, as can be best seen in FIGS. 3 and 9. These facilitate the connection of other fluid-flow devices, as now explained.

One widened-diameter opening portion is on top of insert member 60 and allows insertion of a key portion of overflow chamber assembly 26. Such portion of overflow chamber assembly 26 is inserted into and secured to such widened-diameter opening portion of the insert member 60 in fluid-flow relationship to second port 76.

The other widened-diameter opening portion is laterally located on insert member 60, and allows insertion and securement of sample bottle mounting assembly 30, in fluid-flow relationship to fourth port 80.

When insert member 60 is within shell 58, its tubular lower portion 66 extends through the bottom surface of shell 58 of sampling valve 32. Tubular lower portion also provides a fluid-flow path from reactor vessel 14, including third port 78 in insert member 60.

Figure 7:
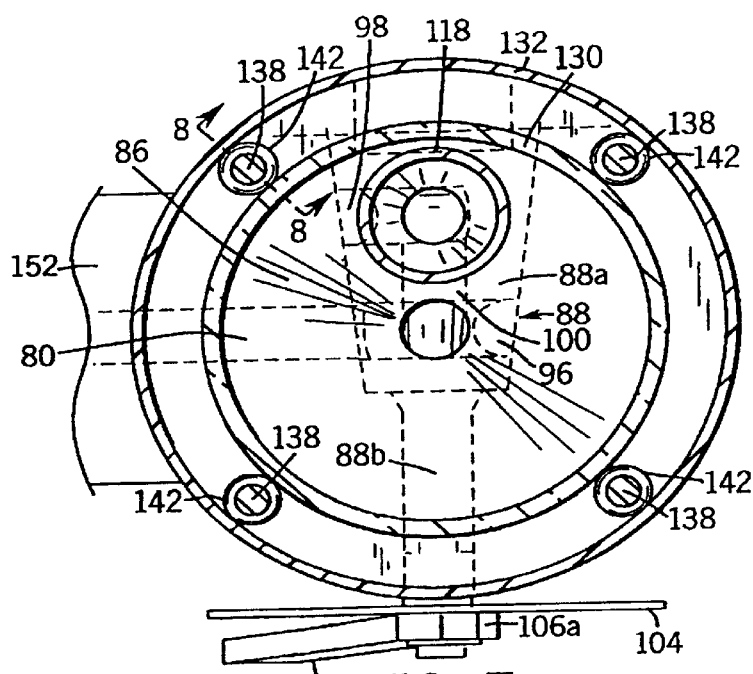
FIG. 7 is a cross-sectional view through the fluid-sampling apparatus, taken along section 7—7 as indicated in FIG. 3.
Figure 8:
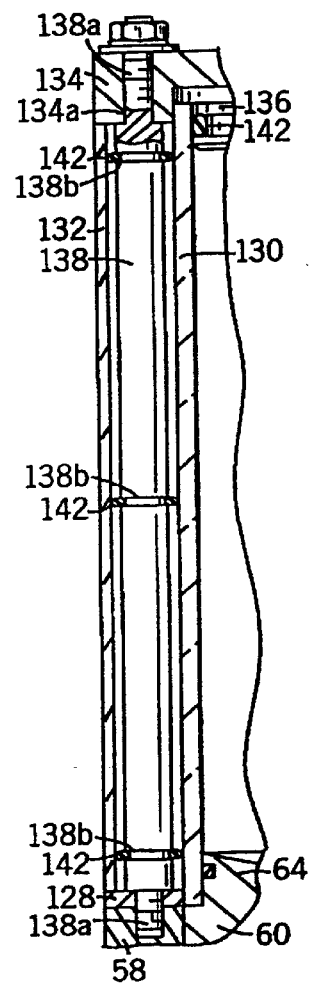
FIG. 8 is a partial cross-sectional view of a tie rod of the fluid-sampling apparatus, taken along section line 8—8 as indicated in FIG. 7.

Upwardly-extending top portion 64 of insert member 60 has a tapered top drain surface 86 which is downwardly tapered toward its middle, as seen in FIG. 7. The angle of taper of tapered top drain surface 86 is preferably about fifteen degrees to facilitate drainage of fluid 12 by gravity from overflow chamber assembly 26.

Figures 3, 9:
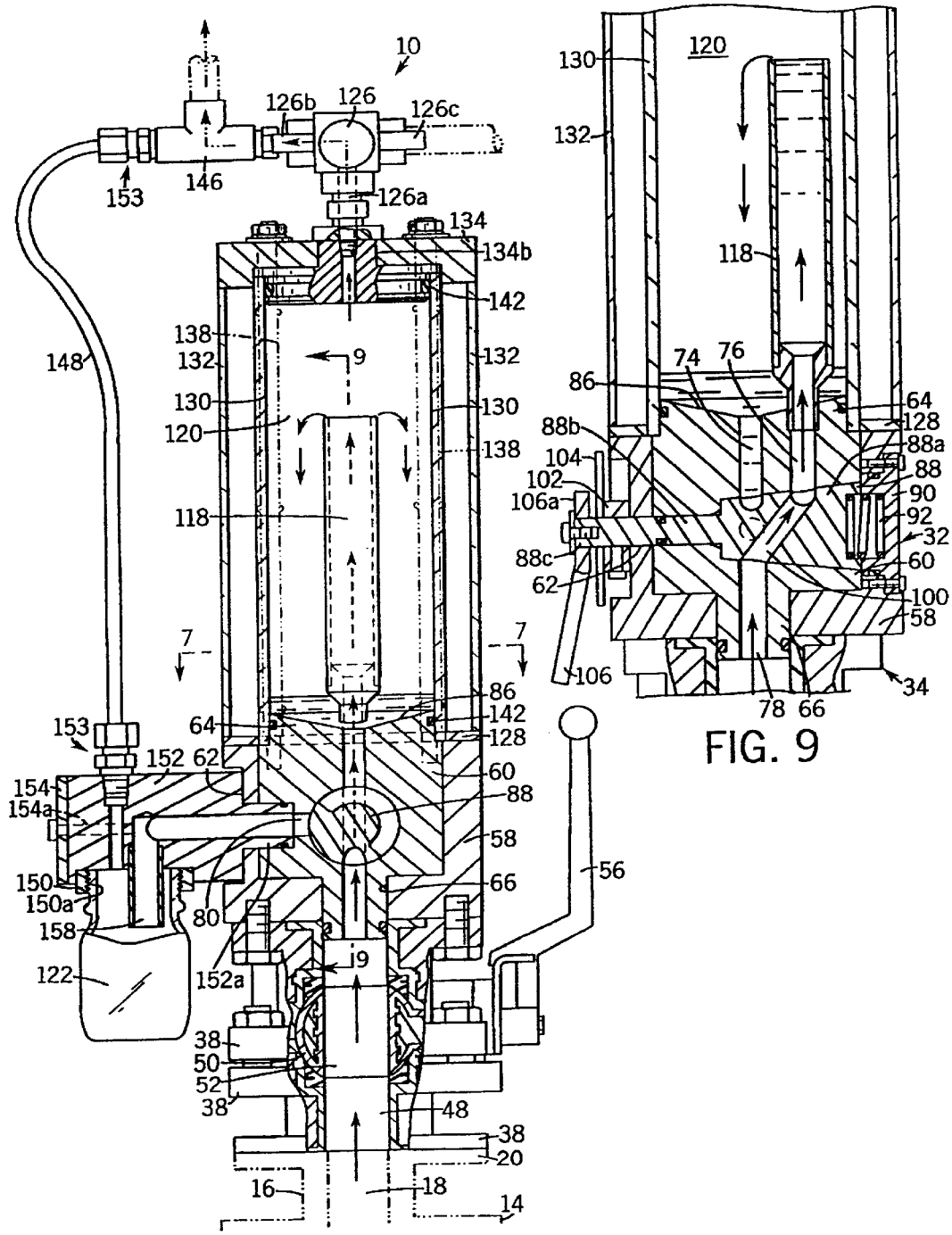
FIG. 3 is a cross-sectional view taken along section 3—3 as indicated in FIG. 2.
FIG. 9 is a partial cross-sectional view through the fluid-sampling apparatus, taken along section 9—9 as indicated in FIG. 3, showing the fluid-sampling apparatus in fill mode wherein fluid can be vacuum drawn from the reactor vessel, through the valve assembly, into the standpipe so as to overflow into the overflow chamber.
Figures 12, 13:
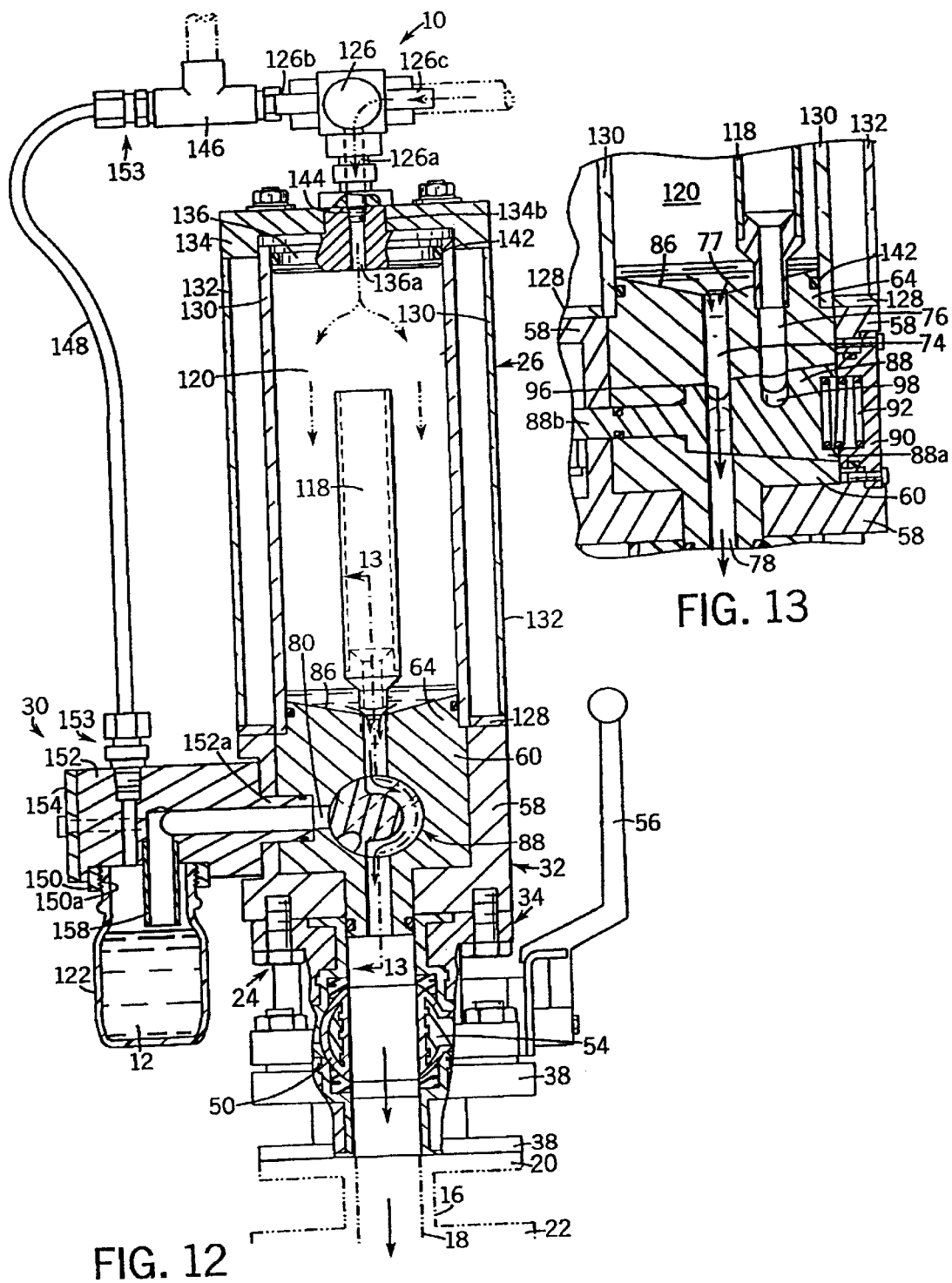
FIG. 12 is a partial cross-sectional view showing the same cross-section as in FIGS. 3 and 10, except that the pivotable valve member has been pivoted so that the apparatus is in the drain mode, allowing fluid in the overflow chamber to either be drained by gravity or purged back to the reactor vessel.
FIG. 13 is a partial cross-sectional view through the fluid-handling apparatus of the present invention, taken along section 13—13 as indicated in FIG. 12.

Referring to FIGS. 9 and 13, the void space within insert member 60 is for housing a pivotable valve member 88. Such void space is joined to the first, second, third and fourth ports 74, 76, 78 and 80 for fluid flow from such space to the periphery of insert member 60. That is, first, second, third and fourth ports 74, 76, 78 and 80 lead from such space to various locations on the outer periphery. First, second, third and fourth ports 74, 76, 78 and 80 are aligned with apertures in the surfaces of shell 58 of sampling valve 32.

Pivotable valve member 88 is slidingly received into the space in insert member 60 such that it is tightly housed therewithin while still able to pivot within insert member 60. This is accomplished by subjecting pivotable valve member 88 to an extremely cold temperature prior to its insertion within the void space within insert member 60. The cold temperature causes pivotable valve member 88, which is preferably made of a Hastelloy® B-2 material, to contract somewhat. While pivotable valve member 88 is still in its contracted state, it is slidingly inserted into the void space within insert member 60. Once pivotable valve member 88 has been inserted into insert member 60, it is allowed to warm up to room temperature so that pivotable valve member 88 expands to fit tightly and precisely within the space within insert member 60. However, despite its tight fit, pivotable valve member 88 is still capable of pivoting within insert member 60.

Figures 10, 11:
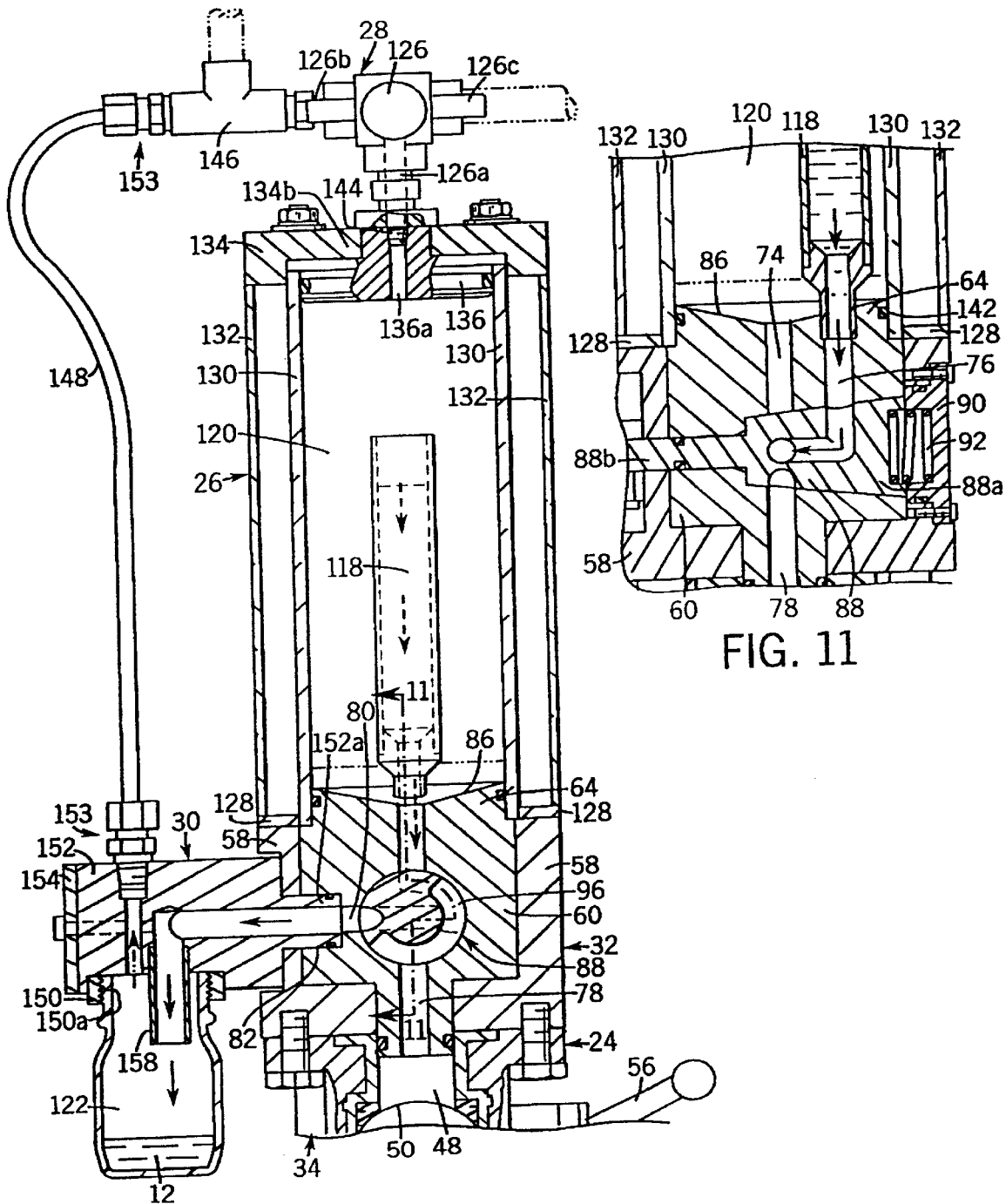
FIG. 10 is a partial cross-sectional view through the fluid-sampling apparatus showing the same cross-section as FIG. 3, except that the pivotable valve member of the fluid-sampling apparatus has been pivoted so that the apparatus is in sampling mode wherein the fluid left in the standpipe can be drained by gravity into the sample bottle.
FIG. 11 is a partial cross-sectional view through the fluid-sampling apparatus, taken along section 11—11 of FIG. 10, showing how the pivotable valve member is spring-loaded within the fluid-sampling apparatus.

Pivotable valve member 88 is preferably spring-loaded within insert member 60 by means of a spring retainer member 90 and spring 92. Referring to FIGS. 9, 11, and 13, the somewhat stepped or two-tiered configuration of spring retainer member 90 is such that spring 92 can be inserted between an indentation in spring retainer member 90 and an indentation in the larger diameter end of main body portion 88*a* of pivotable valve member 88 in order for pivotable valve member 88 to be spring loaded within insert member 60.

Referring to FIGS. 3 and 9–13, ports 74, 76, 78 and 80 through insert member 60 are illustrated. More particularly, first, second and third ports are best seen in FIG. 9, 11, and 13, and the fourth port is best viewed in FIGS. 3, 10, and 12. Ports 74, 76, 78 and 80 lead from an outer peripheral surface of insert member 60 to the space within insert member 60 for housing pivotable valve member 88. Ports 74, 76, 78 and 80 are preferably of a slightly oversized diameter, for instance, approximately nine millimeters. This relatively large diameter and the fact that ports 74, 76, 78 and 80 are relatively short ensures that there is little possibility for them to become plugged up while fluid-sampling apparatus 10 is in operation, even if the fluid being sampled is of high viscosity or has particulate matter therein.

First port 74 is located through the approximate center of tapered top drain surface 86 of upwardly-extending top portion 64 of insert member 60 above the space in insert member 60 occupied by pivotable valve member 88. In other words, first port 74 leads from tapered top drain surface 86 to the space where pivotable valve member 88 is housed within insert member 60.

Second port 76 is parallel to but horizontally offset from first port 74. As already noted, second port 76 leads from a point on tapered top surface 86 to the space within insert member 60 where pivotable valve member 88 is housed. Second port 76 includes a recess 77 of a larger diameter extending downwardly from a point on tapered top surface 86.

Third port 78 extends through the center of tubular lower portion 66 of insert member 60, through the lower portion of insert member 60 to the space within insert member 60 where, as already noted, pivotable valve member 88 is housed within insert member 60.

Finally, fourth port 80 extends through the side of insert member 60 and leads to the space in insert member 60 where pivotable valve member 88 is located.

First, second, third and fourth ports 74, 76, 78, and 80 are open or closed to the passage of fluid 12 therethrough depending upon the orientation of pivotable valve member 88 within insert member 60, as will be explained in more detail below.

Figure 4:
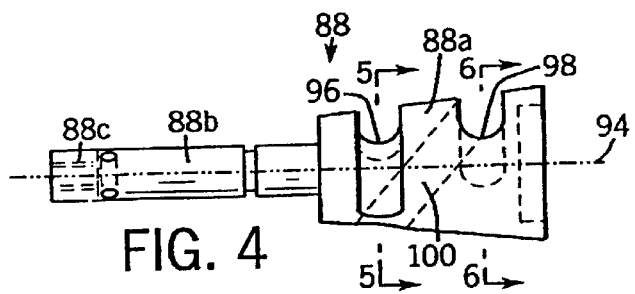
FIG. 4 is a side elevation of a pivotable valve member of the fluid-sampling apparatus.

Referring to FIG. 4, pivotable valve member 88 is made up of first, second and third integral parts 88*a*, 88*b* and 88*c*. The first part or main body portion 88*a* of pivotable valve member 88 is cylindrical in shape and tapers from a first larger diameter end to a second smaller diameter end.

The second part or valve stem portion 88*b* of pivotable valve member 88 is uniformly cylindrical in shape along its length and is smaller in diameter than the diameter of the second smaller diameter end of main body portion 88*a* of pivotable valve member 88. Valve stem portion 88*b* extends between the small diameter end of main body portion 88*a* and the third part or pivot handle portion 88*c*. Pivot handle portion 88*c* is of a typical tab configuration having two parallel sides joined on each end by a radius to receive a like-shaped connection portion of a pivot handle. That is, pivot handle portion 88*c* is of a hockey rink configuration. The diameter between the two radius ends is the same diameter of valve stem portion 88*b*. Pivot handle portion 88*c* includes a threaded bore along the central longitudinal axis 94 of valve member 88 used to secure a pivot handle thereto.

Figure 5:
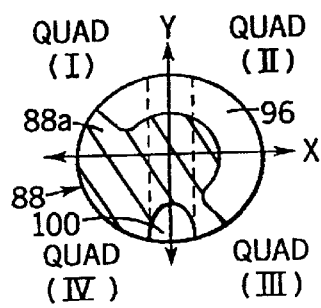
FIG. 5 is a cross-sectional view through the pivotable valve member, taken along section 5—5 as indicated in FIG. 4.

Pivotable valve member 88 has first and second circumferential grooves 96, 98 in an outer periphery of main body portion 88*a* thereof. First circumferential groove 96 is nearer the second smaller diameter end of main body portion 88*a* of pivotable valve member 88. As shown in FIG. 5, first circumferential groove 96 extends for approximately one-hundred-eighty degrees (i.e., from a starting point approximately at a forty-five degree middle of a first quadrant (I), through an entire ninety degrees of a second quadrant (II), and to an ending point at approximately a forty-five degree middle of a third quadrant (III)) around the outer periphery of main body portion 88*a* of pivotable valve member 88.

Figure 6:
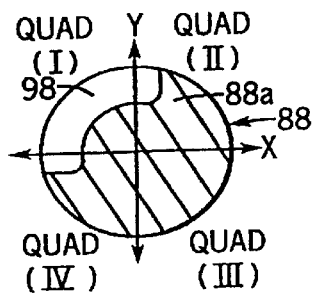
FIG. 6 is cross-sectional view through the pivotable valve member, taken along section 6—6 as indicated in FIG. 4.

Second circumferential groove 98 is nearer the first larger diameter end of main body portion 88*a* of pivotable valve member 88. As shown in FIG. 6, second circumferential groove 98 extends approximately ninety degrees (i.e., from an approximate zero degrees of the first quadrant (I) to an approximate ninety degrees of the first quadrant(I)) around the outer periphery of main body portion 88*a* of pivotable valve member 88.

Pivotable valve member 88 has a diagonal bore 100 through main body portion 88*a* thereof. Diagonal bore 100 extends from the approximate end point of second circumferential groove 98 (see FIG. 4) in the outer periphery of main body portion 88*a* of pivotable valve member 88 (i.e., from an approximate ninety degrees of the first quadrant (I)) to a point (i.e., approximately ninety degrees of the third quadrant (III); see FIG. 5) which is close to the ending point of first circumferential groove 96 in the outer periphery of main body portion 88*a* of pivotable valve member 88 (i.e., an approximate forty-five degrees of the third quadrant (III)).

Referring to FIG. 9, valve stem portion 88*b* and pivot handle portion 88*c* of pivotable valve member 88 extend through front surface of shell 58 of sampling valve 32, through a detent plate 102 and a legend plate 104. A pivot handle 106 is attached to pivot handle portion 88*c* of pivotable valve member 88 by a washer and fastener combination. Detent plate 102 fits in the indentation in the front surface of shell 58 of sampling valve 32 and is of a generally rectangular shape. Detent plate 102 has a central cradle of a size to accommodate valve stem portion 88*b*. The central cradle includes a centrally located half-moon bore portion whose parallel side walls first extend upwardly then extend at an outward angle to a point at the top of detent plate 102. Detent plate 102 includes a threaded bore located centrally on the underside of detent plate 102 extending upwardly and terminating at the bore cradle portion. Detent plate 102 also includes two mounting bores located on either side of the central cradle. Legend plate 104 is a flat, annular member having a central bore through which valve stem portion 88*b* extends and has an outer diameter larger than the indentation in the front surface of shell 58. Legend plate 104 includes inscriptions for three positions thereon, a first position entitled "FILL" which corresponds to a fill mode of fluid-sampling apparatus 10, a second position entitled "DRAIN" which corresponds to a drain mode of fluid-sampling apparatus 10, and a third position entitled "SAMPLE" which corresponds to a sample mode of fluid-sampling apparatus 10. Legend plate 104 includes two mounting bores located on either side of the central bore, such mounting bores align with mounting bores of detent plate 102. Legend plate 104 and detent plate 102 are attached to the front surface shell 58 of sampling valve 32 via fasteners, such as bolts, through the aligned mounting bores and into apertures in the front surface of shell 58.

Pivot handle 106 may be pivoted through an angle of about 90 degrees. When pointer 106a of pivot handle 106 is pivoted so as to point toward the word "FILL" inscribed on legend plate 104 as in FIGS. 1 and 14, pivotable valve member 88 is pivoted so that diagonal bore 100 through pivotable valve member 88 is aligned to connect second port 76 within insert member 60 to third port 78 within insert member 60 as shown in FIG. 9, so that fluid 12 can be drawn, by vacuum or otherwise, from reactor vessel 14 to a first vessel or standpipe 118 to overflow into a second vessel or overflow chamber 120 of overflow chamber assembly 26, as explained in more detail below.

When pointer 106a of pivot handle 106 is pivoted so as to point toward the word "SAMPLE" inscribed on legend plate 104, pivotable valve member 88 is pivoted so that second circumferential groove 98 in the outer periphery of pivotable valve member 88 is aligned to connect second port 76 to fourth port 80 as shown in FIG. 10, so that fluid 12 can drain by gravity from standpipe 118 of overflow chamber assembly 26 to a sample bottle 122 of sample bottle mounting assembly 30. In the alternative, fluid 12 can be pushed via purge connection of three-way valve 126 of vacuum assembly 30 from standpipe 118 of overflow chamber assembly 26 to sample bottle 122.

When pointer 106a of pivot handle 106 is pivoted so as to point toward the word "DRAIN" inscribed on legend plate 104, pivotable valve member 88 is pivoted so that first circumferential groove 96 in the outer periphery of pivotable valve member 88 is aligned to connect first port 74 to third port 78 as shown in FIG. 13, so that fluid 12 can drain by gravity (or if necessary can be pushed via purge connection of three-way valve 126 of vacuum assembly 30 from overflow chamber 120 of overflow chamber assembly 26) to reactor vessel 14.

Referring to FIGS. 1, 2, 3, and 9–14, overflow chamber assembly 26 will now be described in more detail. Overflow chamber assembly 26 includes: a retainer ring 128 for fitting around upwardly-extending top portion 64 of sampling valve 32; a first vessel or standpipe 118 is friction fitted within recess 77 (of second port 76) located at an offset position in tapered top drain surface 86; a second vessel or overflow chamber 120 which is formed by a transparent, borosilicate glass tube 130 (as its sidewall), and retainer ring 128 and tapered top surface 86 of upwardly-extending top portion 64 (as its bottom surface); a transparent, outer protective plastic tubular covering 132 surrounding glass tube 130; an upper ring member 134 with an upper insert member 136 fitted at least partially therewithin for acting as a cover or top for overflow chamber 120; and a plurality of tie rods 138 for tying upper ring member 134 to the top of sampling valve 32.

Retainer ring 128 sits atop shell 58 of sampling valve 32. Upwardly-extending top portion 64 of insert member 60 extends vertically upwardly past the top of retainer ring 128, as shown in FIGS. 1 and 2. Upwardly-extending top portion 64 has a circumferential groove 140 in its sidewall to accept an O-ring 142 which acts as a seal against the inner periphery of glass tube 130.

Tie rods 138, preferably made of stainless steel, are used to connect valve assembly 24 to upper ring member 134 of overflow chamber assembly 26. The plurality of tie rods 138 are adjacent to the outer periphery of glass tube 130. Each tie rod 138 has first and second threaded ends 138a. First ends 138a mate with threaded apertures 144 in the top of insert member 60. Second threaded ends 138a extend through non-threaded apertures in upper ring member 134; nuts are secured to second threaded ends 138a to fasten upper ring member 134 and upper insert member 136 as a cover over overflow chamber assembly 26.

Tie rods 138 have spaced circumferential grooves 138b along a length thereof. Grooves 138b are for acceptance of O-ring members 142 to serve as protective spacers between tie rods 138 and the outer periphery of precision-ground glass tube 130 and the inner periphery of outer plastic protective covering 132.

Transparent tube 132, made of plastic, preferably acrylic, is placed around glass tube 130 to act as a protective cover.

Standpipe 118 is an inner first vessel housed within outer second vessel or overflow chamber 120, which is formed by glass tube 130 and the other nearby structure. Standpipe 118 has an open top with a large opening and an open bottom with a smaller opening. Standpipe 118 has a tapered inside bottom surface which allows standpipe 118 to drain easily and completely by gravity. Standpipe 118 has a transparent tube portion and funnel-like bottom portion. The bottom portion of standpipe 118 terminates in an outlet tube of a narrower diameter which is friction fit into recess 77 of second port 76 in insert member 60. Standpipe 118 stands upright on insert member 60.

An upper ring member 134 has a plurality of holes 134a therethrough, preferably four evenly spaced approximately ninety degrees apart, for acceptance of threaded ends 138a at the top of tie rods 138 therethrough. Holes 134a are preferably situated so as to be at a distance approximately equal to the thickness of plastic tubular covering 132 from the outer periphery of upper ring member 134. There is a stepped aperture 134b at the center of upper ring member 134. In other words, near the top surface of upper ring member 134, there is an aperture of a first, smaller diameter. The aperture of the first, smaller diameter only goes through about half the thickness (i.e., the top half) of upper ring member 134 and leads to an aperture of a second, larger diameter which is adjacent the lower surface of upper ring member 134, and which also only goes through about half (i.e., the lower half) of the thickness of upper ring member 134. This stepped aperture 134b is used to partially house upper insert member 136.

Upper insert member 136 is a somewhat stepped, annular member having a lower portion of a diameter approximately equal to or slightly smaller than the second, larger diameter of stepped aperture 134b of upper ring member 134 so that at least an upper portion of the lower portion of upper insert member 136 fits within the second, larger diameter of stepped aperture 134b of upper ring member 134. Upper insert member 136 also has an upper portion of a diameter approximately equal to or slightly smaller than the first, smaller diameter of stepped aperture 134b of upper ring member 134 in order that at least a lower portion of the upper portion of upper insert member 136 fits within the first, smaller diameter of stepped aperture 134b of upper ring member 134.

As best seen on FIGS. 10 and 12, upper insert member 136 has a cylindrical aperture 136a at a center thereof. The upper portion of cylindrical aperture 136a includes a tapered, threaded portion for mating with a threaded tube 144 leading from a first port or vacuum/purge inlet 126a of three-way valve 126 of vacuum assembly 28.

The preferred embodiment of fluid-sampling apparatus 10 of the present invention has a vacuum assembly 28. Fluid-sampling apparatus 10 may also be used on reactor tanks or vessels that operate at a positive pressure of 90 psi (i.e., 6 bar), in which case, vacuum assembly 28 would not be needed, but some external valving modifications would be required.

When a vacuum assembly 28 is used, the vacuum assembly would include a three-way valve 126 having: a first port or vacuum/purge inlet 126a threadingly connected to upper insert member 136 of overflow chamber assembly 26; a second port 126b connected to a vacuum connection 146, which is in turn connected to a vacuum source; and a third port 126c being connectable, if necessary, to a flush/purge connection and a flush/purge source. Vacuum assembly 28 would also include Teflon hose or other tubing 148 leading from vacuum connection 146 to sample bottle mounting assembly 30.

Sample bottle mounting assembly 30 includes: sample bottle 122; a sample bottle adapter 150; sample bottle mounting block 152; and a sample bottle mount support plate 154.

Sample bottle mounting block 152 has a laterally-extending tubular male portion 152a received within a lateral female receptacle in insert member 60, so that sample mounting block 152 is in fluid-flow engagement with fourth port 80 in insert member 60. In this way, sample bottle mounting block 152 is mounted to the side of sampling valve 32 in a cantilever fashion. Such mounting is between upper and lower flanges on the outside periphery of shell 58.

The inner diameter of tubular male portion 152a coincides with a port leading to sample bottle dip tube 158. Sample bottle dip tube 158 passes through sample bottle adapter 150 and into sample bottle 122.

Sample bottle mounting block 152 also includes a port through the height of mounting block 152 leading from the top surface thereof to a top surface of an aperture within the bottom of mounting block 152. The aperture is for friction-fit acceptance of sample bottle adapter 150. A port through the height of mounting block 152 has a top portion which is tapered and threaded for mating acceptance of a compression fitting 153 for connection of tubing 148 leading from vacuum connection 146, It should be noted that sample bottle 122 is vented in such a way that any vapors released from the sample of fluid 12 in sample bottle 122 are returned to overflow chamber 120 of overflow chamber assembly 26.

Sample bottle adapter 150 is an annular member having a female threaded aperture 150a at the center thereof for threadingly mating with a male threaded open end of sample bottle 122. Sample bottle adapter 150 is held suspendedly from sample bottle mounting block 152 by a friction fit mount or equivalent.

Sample bottle mount support plate 154 is generally square and has at least two holes 154a through a thickness thereof, holes 154a being for acceptance of fasteners, most preferably bolts, for securing mounting block 152 to the side of sampling valve 32.

Fluid-sampling apparatus 10 of the present invention which is made of the above-described parts is easily flushed for cleaning out the internal workings thereof. Furthermore, fluid-sampling apparatus 10 is easy to disassemble for replacement of worn or damaged parts. Pivotable valve member 88 of fluid-sampling apparatus 10 is designed so that if cross-flow leakage occurs within sampling valve 32 due to valve misalignment, there is no consequence on the representivity of sample of fluid 12. This is because the head or height of the fluid in standpipe 118 is always higher than the head or height of fluid 12 in overflow chamber 120. Thus, even if there is cross-flow leakage, it is always from a contemporaneous sample of fluid 12 to an old sample of fluid 12 so that contamination is prevented.

Figure 14:
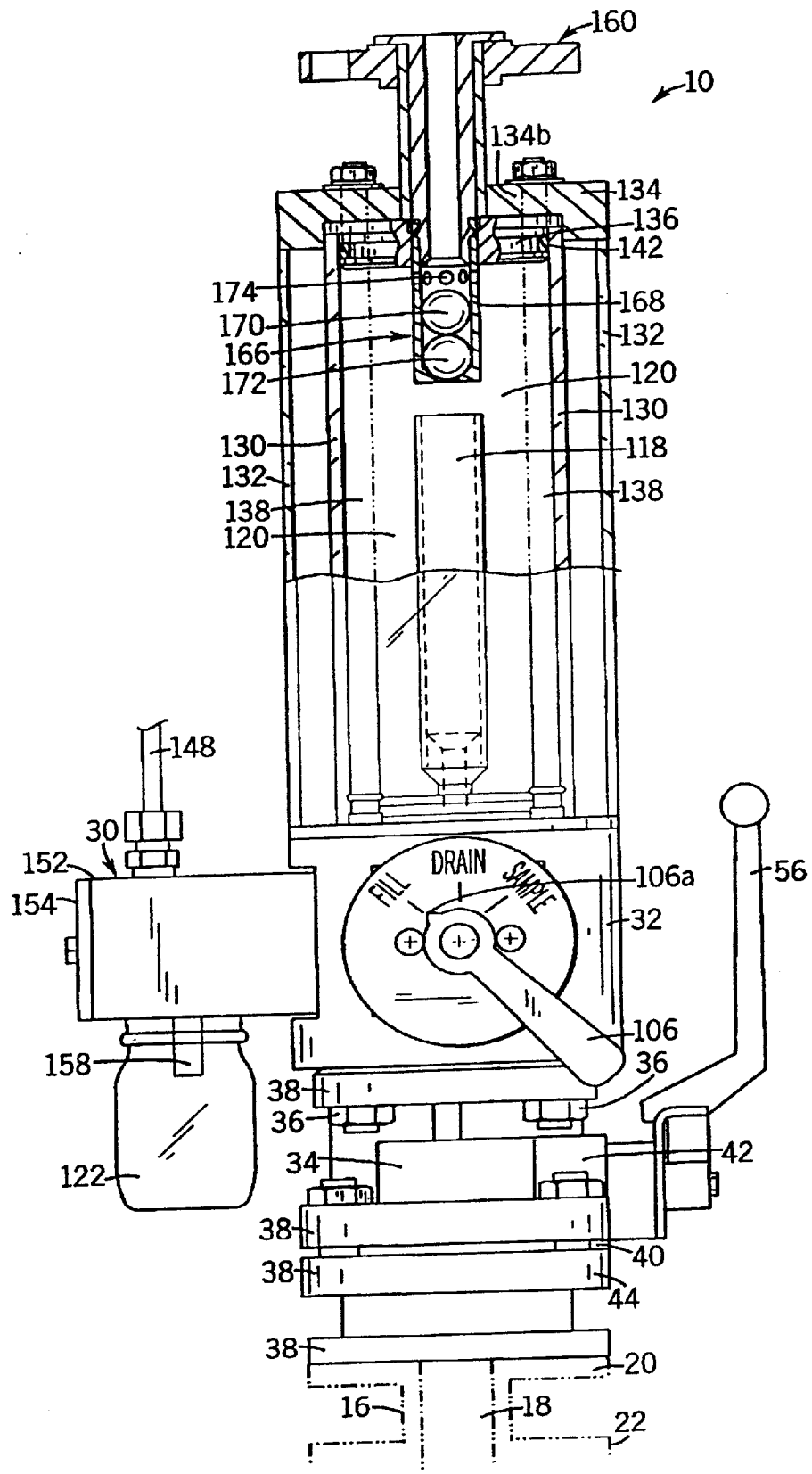
FIG. 14 is a front elevational view, partially in second, showing a second embodiment of the fluid-sampling apparatus of the present invention.

Referring to FIG. 14, a second embodiment of fluid-sampling apparatus 10 of the present invention is illustrated. In the second embodiment, a ball check valve 166 is suspended from upper insert member 136 at least partially housed within upper ring member 134. Ball check valve 166 has a central tubular member 168 which contains a first upper floatable ball 170 and a second, lower floatable ball 172 therein. The central tubular member 168 has small apertures 174 evenly spaced around the outer periphery thereof at a height from the bottom of central tubular member 168 approximately equal to twice the diameter of one of balls 170, 172. In this way, upper floatable ball 170 never touches fluid 12 being vacuum-drawn from reactor vessel 14, because as lower floatable ball 172 rises with the fluid level, it pushes upper floatable ball 170 upwardly until upper floatable ball 170 passes small apertures 174 and cuts off the vacuum, sealing the overflow chamber 120 and preventing fluid 12 from getting into and contaminating the first port or vacuum/purge inlet 126a of three way valve 126.

In operation, fluid-sampling apparatus 10 of the present invention is designed to sample fluid 12 from a reactor vessel 14. Reactor vessel 14 may be used, for example, for pharmaceutical applications in which a large vessel is needed for mixing and reacting compositions for manufacture of various drugs.

Fluid-sampling apparatus 10 of the present invention generally works as follows:

Initially, ball valve 34 of valve assembly 24 is closed and sampling valve 32 is in drain mode, where it was at the end of the last fill-sample-drain cycle. Handle 106 of sampling valve 32 is in a position so that pointer 106a on handle 106 of sampling valve 32 points toward the word "DRAIN" on legend plate 104 and pivotable valve member 88 is in the drain position wherein the first or central upper port 74 of sampling valve 32 is connected to the third or central lower port 78 of sampling valve 32 via first circumferential groove 96 in the outer periphery of pivotable valve member 88.

To begin a new cycle, handle 56 of ball valve 34 is pivoted so that ball valve 34 is opened. Then, handle 106 of sampling valve 32 is pivoted until pointer 106a of handle 106 of sampling valve 32 points towards the word "FILL." When three-way valve 126 is opened to vacuum connection 146 so that when the vacuum source is turned on, fluid 12 is drawn upwardly from reactor vessel 14 through dip tube 18 situated in sampling port 16, through ball valve 34, through the third or central lower port 78 in sampling valve 32, through diagonal bore 100 in pivotable valve member 88 of sampling valve 32, through the second or upper, horizontally-offset port 76 in sampling valve 32 and into standpipe 118.

As fluid 12 continues to be drawn upwardly, it eventually fills standpipe 118, begins to overflow from standpipe 118, and collects in overflow chamber 120. The pressure differential between standpipe 118 and overflow chamber 120 ensures that fluid 12 drawn from reactor vessel 14 does not flow into vacuum assembly 28, but instead drops to the bottom of overflow chamber 120. The pressure differential between standpipe 118 and overflow chamber 120 is due in part to the relative difference in their volumetric capacities. More particularly, standpipe 118 is capable of holding a liquid volume capacity of approximately sixty milliliters, whereas overflow chamber 120 is capable of holding a liquid volume capacity of approximately one liter. In the second embodiment, ball check valve 166 also helps to ensure that fluid 12 being drawn from reactor vessel 14 is not drawn into vacuum assembly 28.

When fluid 12 in overflow chamber 120 is about two-thirds the height of standpipe 118, which can be observed through the transparent walls of the overflow chamber, vacuum connection 146 is closed and ball valve 34 is closed so that no more fluid 12 can be drawn from reactor vessel 14. Fluid 12 in standpipe 118 is the end flow product—an accurately representative sample from the reactor vessel, because all of the "dead sample" has overflowed into overflow chamber 120.

Since standpipe 118 has a volume of approximately sixty milliliters and overflow chamber 120 has an approximate volume of one liter, the volume of fluid 12 needed to be overflowed from dip tube 18 to overflow chamber 120 can be calculated by determining the volume of sample in dip tube 18. This volume is multiplied by two or three to arrive at the overflow volume required. Then the height can be marked on outer plastic covering 132 of overflow chamber assembly 26 and the vacuum source can be shut off when fluid 12 in overflow chamber 120 reaches this height. Through experimentation, applicants have learned that overflow volume of half the height of dip tube 18 is sufficient to receive a properly representative sample of fluid 12 in standpipe 118.

Handle 106 of sampling valve 32 is then pivoted so that pointer 106a of handle 106 of sampling valve 32 is pointing towards the word "SAMPLE" inscribed on legend plate 104. This in turn rotates pivotable valve member 88 within insert member 60 of sampling valve 32 from its position wherein diagonal bore 100 of pivotable valve member 88 is in fluid-flow connection with (a) the third or lower central port 78 of sampling valve 32 and (b) the second or upper horizontally-offset port 76, and to the position in which second circumferential groove 98 of pivotable valve member 88 is in fluid-flow connection with (a) the second or upper horizontally-offset port 76 (leading from standpipe 118) and (b) the fourth or side port leading to sample bottle 122, so that the sample of fluid 12 in standpipe 118 is allowed to drain by gravity into sample bottle 122.

Although fluid-sampling apparatus 10, when in the sample mode, is designed to move fluid from standpipe 118 to sample bottle 122 by gravity flow, a vacuum may be applied via vacuum connection 146 and tubing 148 or pressurizing overflow chamber 120 via three-way valve 126 may also be used to help sample of fluid 12 from standpipe 118 to flow to sample bottle 122, if necessary due to the high viscosity of fluid 12 or otherwise. This provides an alternative to gravity flow.

It should be noted that the volumetric capacity of standpipe 118 is only about 80 percent of the volumetric capacity of sample bottle 122. This ensures that sample bottle 122 cannot become overfilled by fluid 12 drained from standpipe 118.

Next, handle 106 of sampling valve 32 is pivoted so that pointer 106a points toward the word "DRAIN" inscribed on legend plate 104, and handle 56 of ball valve 34 is pivoted so that ball valve 34 is opened. Pivotable valve member 88 is oriented such that its first circumferential groove 96 is in fluid-flow alignment with the first (or upper central) and third (or lower central) ports 74 and 78 in insert member 60, so that the fluid overflowed from standpipe 118 into overflow chamber 120 can be drained by gravity back into reactor vessel 14.

Although the fluid-sampling apparatus 10 of the present invention, when in the drain mode, is designed to drain by gravity, three-way valve 126 may also be used to pressurize overflow chamber 120 to help push overflowed fluid 12 in overflow chamber 120 back into reactor vessel 14. This provides an alternative means of draining.

Design and operation of fluid-sampling apparatus 10 is such that only corrosion-resistant materials (e.g., borosilicate glass, virgin Teflon, and Hastelloy®) come into contact with the reaction fluid. This is desirable because fluid 12 in reactor. vessel 14 may be corrosive.

Figure 15:
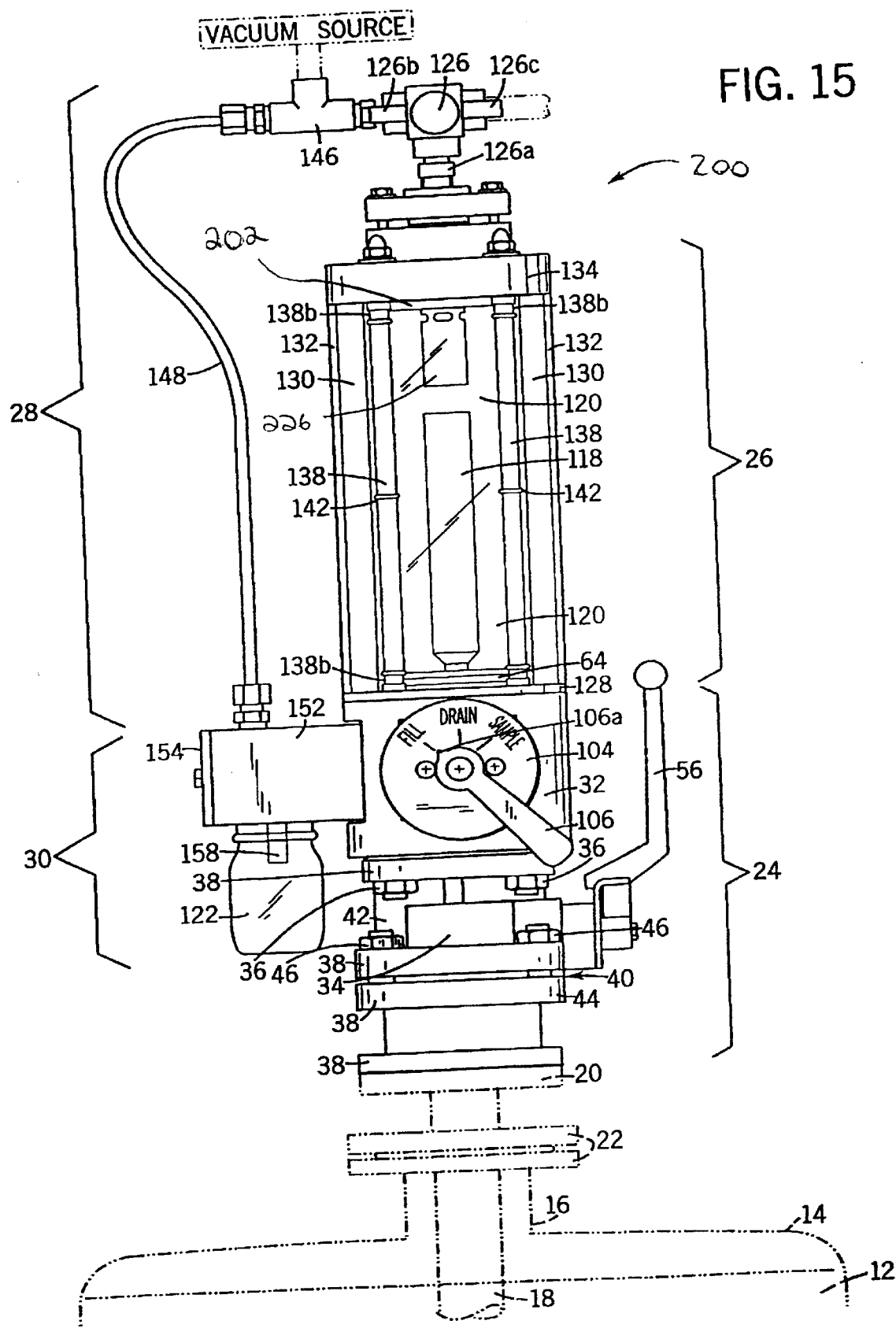
FIG. 15 is a front elevational view of a third embodiment of the fluid-sampling apparatus of the present invention.
Figure 16:
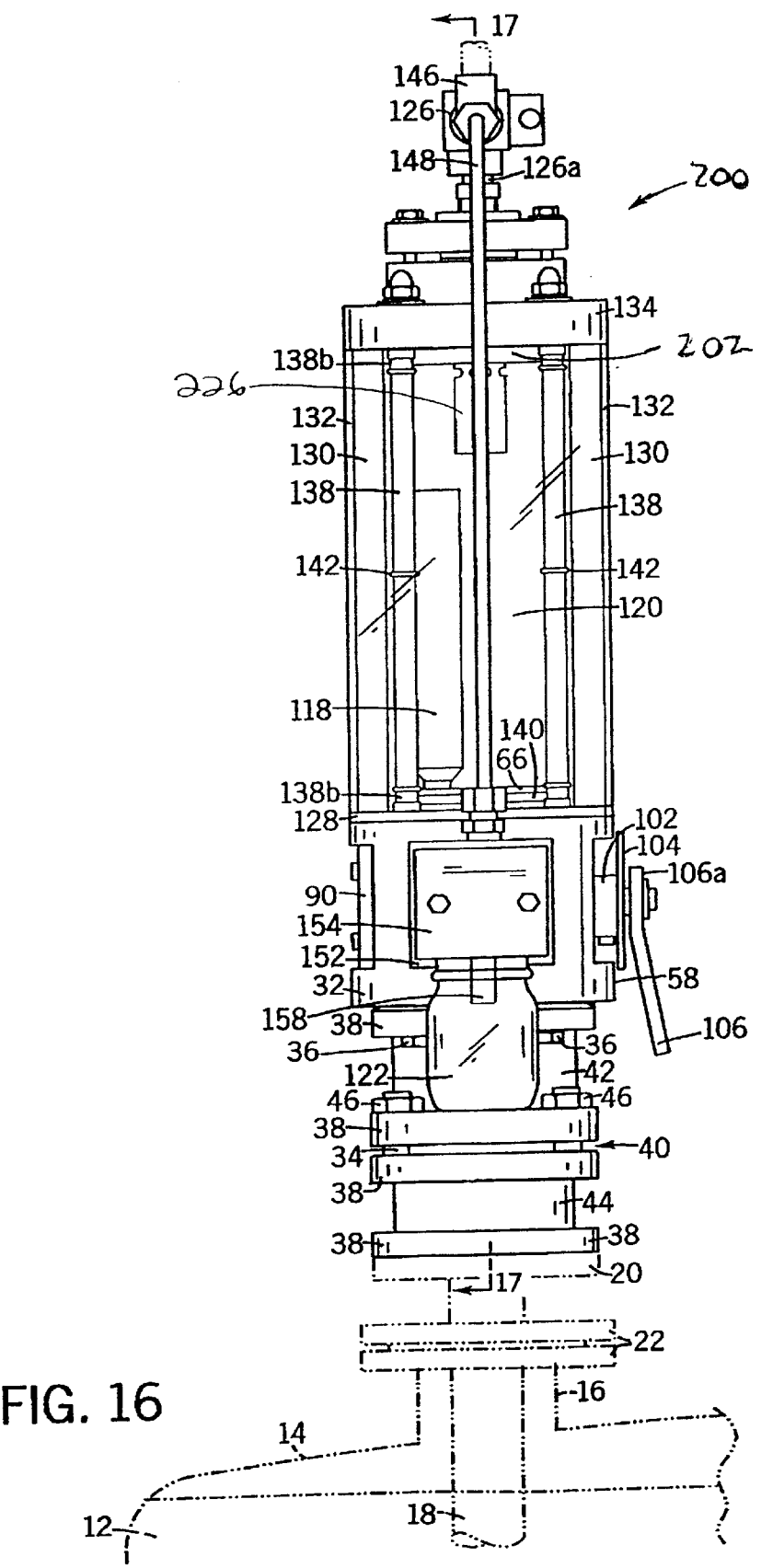
FIG. 16 is a side elevational view of the fluid-sampling apparatus of FIG. 15.

Referring to FIG. 15, an alternate embodiment of the fluid-sampling apparatus is generally designated by the reference numeral 200. Fluid-sampling apparatus 200 is substantially identical to fluid-sampling apparatus 10, except as hereinafter provided. As such, the prior description of fluid-sampling apparatus 10 is understood to describe the common portions of fluid-sampling apparatus 200 as if fully described herein with common reference characters being used.

In fluid-sampling apparatus 200, overflow chamber assembly 26 includes an alternate upper insert member 202 which is at least partially housed within upper ring member 134. Upper insert member 202 includes a lower end 204 and an upper end 206. A sealing flange 208 projects radially from upper end 206 of upper insert member 202. Sealing flange 208 includes a circumferentially extending groove 210 therein. Sealing flange 208 is captured between the upper end of glass tube 130 and upper ring member 134 so as to form a seal therebetween.

Upper insert member 202 further includes a radially outer surface 212 which is directed towards the inner surface of glass tube 130. In addition, upper insert member 202 includes a radially inner surface 214 which defines an opening therethrough. The opening in upper insert member 202 is axially aligned with corresponding opening in upper ring member 134.

Seal 216 is disposed within a groove along the radially inner surface 214 of upper insert member 202 adjacent upper end 206 thereof. Seal 216 forms a sealing interface with the outer surface 218 of a float valve flange insert 220. Float valve flange insert 220 includes an upper end 224 having an enlarged head which is seated in a corresponding groove formed in upper ring member 134 and a second, opposite threaded end 224 received within the opening in upper insert member 202.

Float ball cage 226 is threaded onto the threaded end 224 of float valve flange insert 220 so as to depend therefrom into overflow chamber 120. Float valve flange insert 220 includes a passageway 228 which is coincident with a passageway 230 defined by float valve ball cage 226.

Upper and lower float balls 234 and 236 are disposed within the passageway 230 defined by float valve ball cage 226. Float valve ball cage 226 includes a plurality of circumferentially spaced vacuum ports 238 circumferentially spaced about the upper end thereof and fill/drain ports 240 in the lower end thereof. It is noted that a valve seat 242 is provided in the lower end 224 of float valve flange insert 220 for accommodating upper float ball 234 in a sealing relationship, as hereinafter described.

In order for passageway 228 in float valve flange insert 220 to communicate with the interior of threaded tube 144, utilities flange 246 is provided. The utility flange 246 is bolted onto upper ring member 134 by bolts 248 and includes a central passageway 250 which is coincident with passageway 228 through float valve flange insert 220 and the interior of threaded tube 244.

Figure 17:
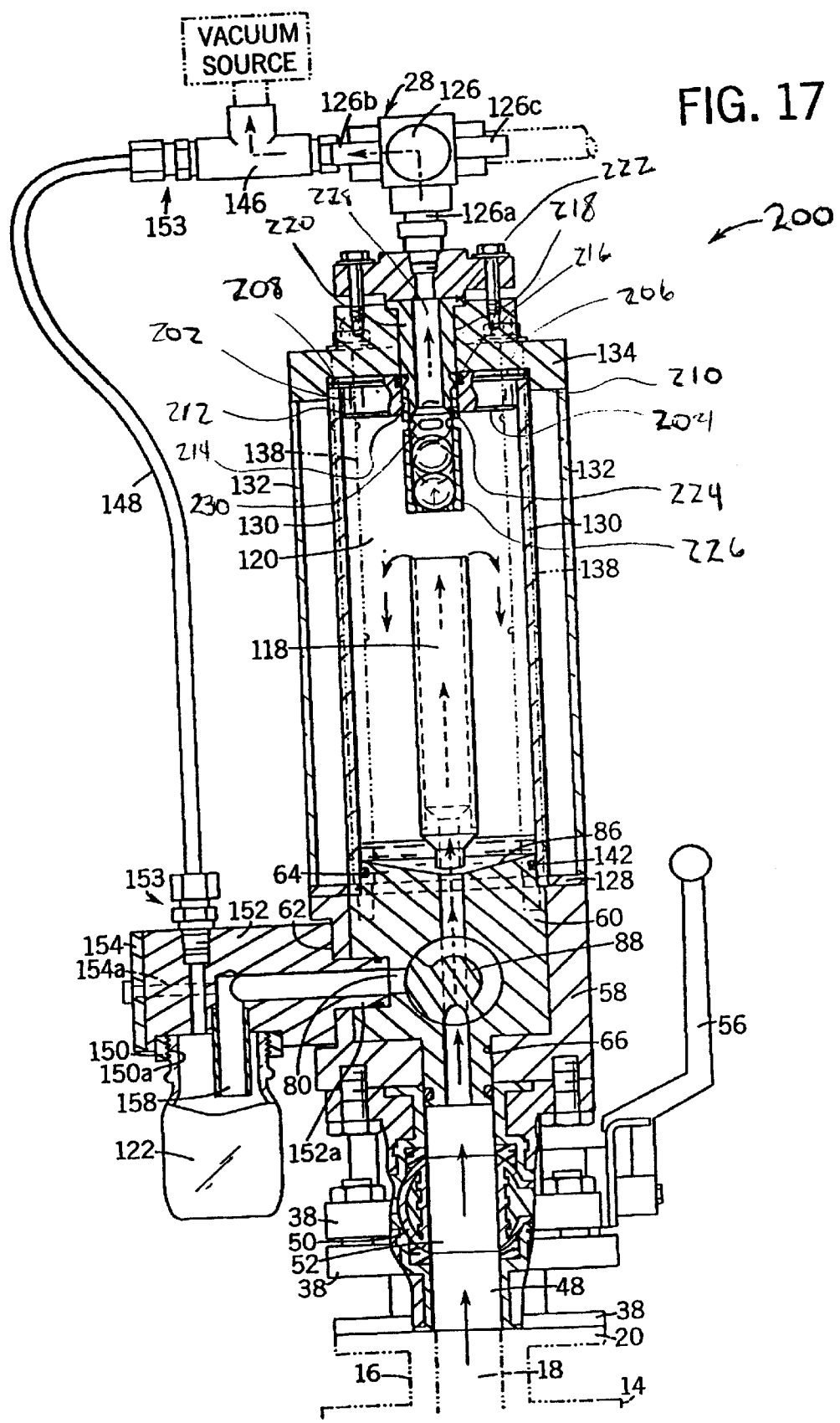
FIG. 17 is cross sectional view of the fluid-sampling apparatus of the present invention taken along line 17—17 of FIG. 16.
Figure 18:
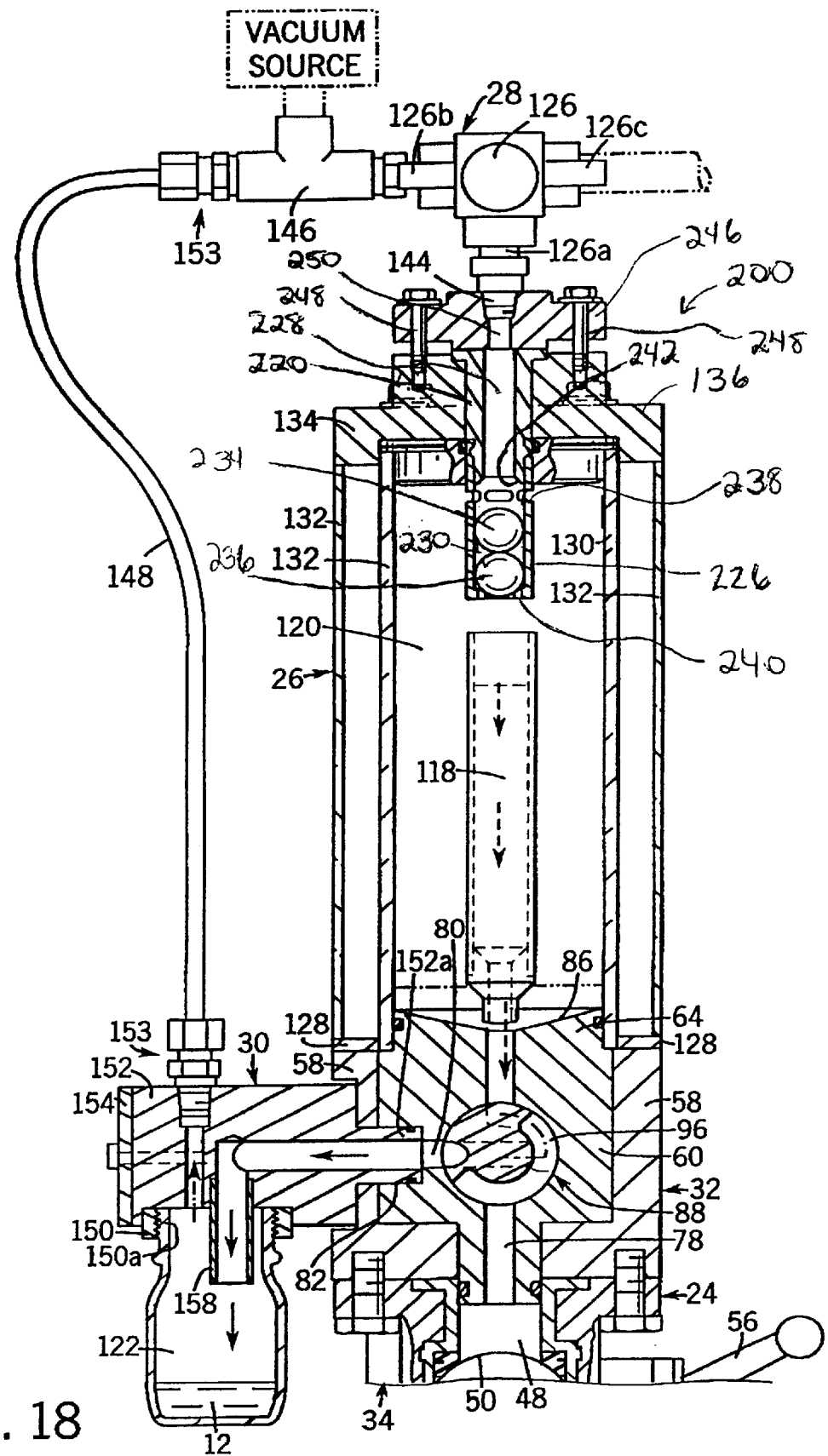
FIG. 18 is a cross-sectional view, similar to FIG. 17, showing the fluid-sampling apparatus of the present invention with the pivotable valve in the sampling position.
Figure 19:
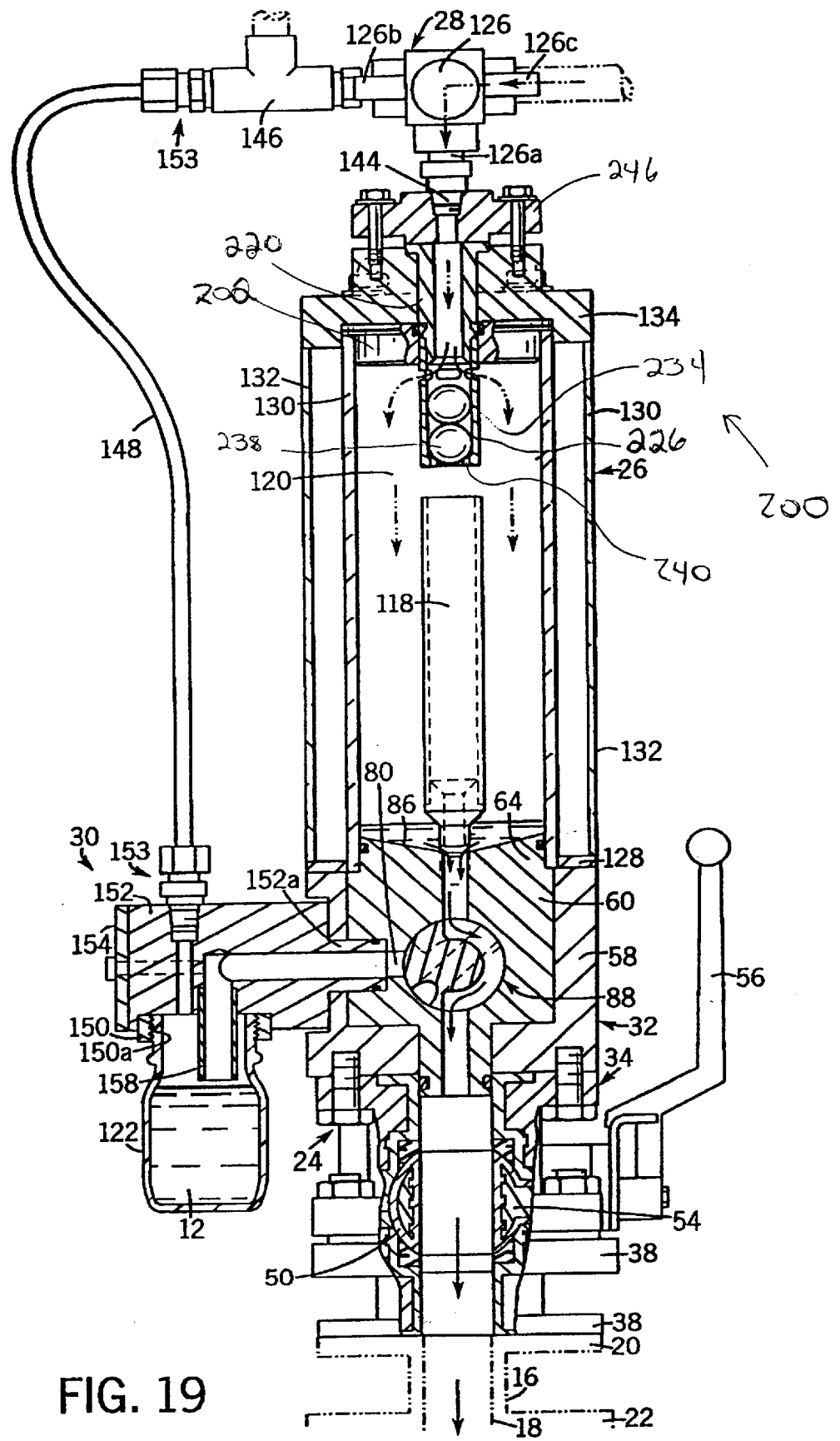
FIG. 19 is a cross-sectional view, similar to FIG. 17, showing a fluid-sampling apparatus of the present invention with the pivotable valve in the drain position.

In operation, the vacuum source communicates with overflow chamber 120 through vacuum ports 238. As the vacuum source draws fluid into the overflow chamber 120, FIG. 17, as heretofore described, the fluid level rises in overflow chamber 120. As the fluid level rises within overflow chamber 120, the fluid passes through the fill/drain ports 240 in float valve ball cage 226 and into contact with lower float ball 236. As overflow chamber 120 continues to fill, the fluid therein urges lower float ball 236 upwardly within float valve ball cage 226 such that upper float ball 234 becomes seated within valve seat 242 at the lower end of float valve flange insert 220, shown in phantom in FIG. 17. As a result, upper float ball 234 isolates the vacuum source from the overflow chamber 120 so as to prevent the further drawing of fluid therein.

Various modes of carrying out the invention are contemplated as being within the scope of the following claims particularly pointing out and distinctly claiming the subject matter which is regarded as the invention.

We claim:

1. A vacuum assembly for drawing fluid into an interior of an overflow tank from a fluid source, comprising:
    a vacuum source;
    a tubular conduit having a first end operatively connected to the vacuum source and a second end disposed within the overflow tank; and
    an overflow element for preventing the flow of fluid into the conduit in response to fluid in the overflow tank reaching a predetermined level.

2. The vacuum assembly of claim 1 wherein the conduit includes a vacuum port spaced from the second end of the conduit.

3. The vacuum assembly of claim 2 wherein the conduit includes a fill port at the second end of the conduit.

4. The vacuum assembly of claim 3 wherein the overflow element is positioned within the conduit, the overflow element movable between a fill position wherein the vacuum source communicates with the interior of the overflow tank and a shut-off position wherein the interior of the overflow tank is isolated from the vacuum source.

5. The vacuum assembly of claim 4 wherein overflow element is urged from the fill-position to the shut-off position by fluid in the interior of the overflow tank.

6. The vacuum assembly of claim 4 wherein the overflow element includes a float ball.

7. A fluid-sampling apparatus for sampling fluid from a fluid source, comprising:
    an overflow chamber assembly defining an overflow chamber therein;
    a valve assembly interconnecting the overflow chamber assembly and the fluid source, the valve assembly including a valve movable between a first position wherein the overflow chamber communicates with the fluid source and a second position; and
    a vacuum assembly connected to the overflow chamber assembly for drawing fluid from the fluid source into the overflow chamber through the valve, the vacuum assembly including a float valve cage disposed within the overflow chamber for limiting the fluid drawn into the overflow chamber to a predetermined level.

8. The fluid-sampling apparatus of claim 7 wherein the vacuum assembly includes a tubular conduit having a first end operatively connected to a vacuum source and a second end operatively connected to the float valve cage.

9. The fluid-sampling apparatus of claim 8 further comprising a seal having a central aperture for allowing the tubular conduit to pass therethrough, the seal having a sealing flange projecting radially from the central aperture.

10. The fluid-sampling apparatus of claim 9 wherein the sealing flange is captured between the vacuum assembly and the overflow chamber assembly.

11. The fluid-sampling apparatus of claim 7 wherein the flow valve cage includes a vacuum port.

12. The fluid-sampling apparatus of claim 11 wherein the float valve cage includes an overflow element disposed therein, the overflow element movable between a fill position wherein a vacuum source communicates with the interior of the overflow chamber through the vacuum port and a shut-off position wherein the interior of the overflow chamber is isolated from the vacuum source.

13. The fluid-sampling apparatus of claim 12 wherein overflow element is urged from the fill position to the shut-off position by fluid in the overflow chamber.

14. The fluid-sampling apparatus of claim 12 wherein the overflow element is a float ball.

15. A fluid-sampling apparatus for sampling fluid from a fluid source, comprising:
    an overflow chamber assembly defining an overflow chamber therein;
    a valve assembly interconnecting the overflow chamber assembly and the fluid source, the valve assembly including a valve movable between a first position wherein the overflow chamber communicates with the fluid source and a second position;
    a vacuum assembly connected to the overflow chamber assembly for drawing fluid from the fluid source into the overflow chamber through the valve, the vacuum assembly including a float valve cage disposed within the overflow chamber for limiting the fluid drawn into the overflow chamber to a predetermined level; and
    a sample bottle having an interior and being operatively connected to the valve assembly wherein the interior of the sample bottle communicates with the overflow chamber with the valve in the second portion.

16. The fluid-sampling apparatus of claim 15 wherein the float valve cage includes a vacuum port.

17. The fluid-sampling apparatus of claim 16 wherein the float valve cage includes an overflow element disposed therein, the overflow element movable between a fill position wherein a vacuum source communicates with the interior of the overflow chamber through the vacuum port and a shut-off position wherein the interior of the overflow chamber is isolated from the vacuum source.

18. The fluid-sampling apparatus of claim 17 wherein overflow element is urged from the fill portion to the shut-off position by fluid in the overflow chamber.

19. The fluid-sampling apparatus of claim 17 wherein the overflow element includes first and second float balls.

* * * * *